United States Patent [19]

Toole, Jr.

[11] Patent Number: 4,868,112

[45] Date of Patent: Sep. 19, 1989

[54] NOVEL PROCOAGULANT PROTEINS

[75] Inventor: John J. Toole, Jr., Jamaica Plain, Mass.

[73] Assignee: Genetics Institute, Inc., Cambridge, Mass.

[21] Appl. No.: 10,085

[22] PCT Filed: Apr. 11, 1986

[86] PCT No.: PCT/US86/00774

§ 371 Date: Apr. 11, 1986

§ 102(e) Date: Apr. 11, 1986

[87] PCT Pub. No.: WO86/06101

PCT Pub. Date: Oct. 23, 1986

Related U.S. Application Data

[63] Continuation-in-part of Ser. No. 725,350, Apr. 12, 1985, abandoned.

[51] Int. Cl.$^4$ ........................ C12P 21/00; C12P 21/02; C12N 15/00; C07H 15/12

[52] U.S. Cl. ........................................ 435/68; 435/70; 435/172.3; 435/240.1; 435/240.2; 435/320; 435/948; 435/252.33; 530/383; 536/27; 514/2; 514/8

[58] Field of Search ................ 435/68, 70, 172.3, 253, 435/255, 256, 240.1, 240.2, 320; 530/383; 534/27; 935/11, 32, 34, 56, 57, 60, 70; 514/2, 8

[56] References Cited

PUBLICATIONS

Wood et al, *Nature,* vol. 312, 22 Nov. 1984, pp. 330–336, "Expression of Active Human Factor VIII from Recombinant DNA Clones".

Toole et al, *Nature,* vol. 312, 22 Nov. 1984, pp. 342–347, "Molecular Cloning of a cDNA Encoding Human Antihaemophilic Factor".

Vehar et al, *Nature,* vol. 312, 22 Nov. 1984, pp. 337–342, "Structure of Human Factor VIII".

Orr et al, *Thrombos Haemostasis,* vol. 57(1), p. 57, 1985, "Spacer Function Imp for the Heavily Glycosylated Region of Factor VIII".

Toole et al, *Proc. Natl. Acad. Sci.,* vol. 83, pp. 5939–5942, Aug. 1986, "A Large Region ($\approx$95 kDa) of Human Factor VIII is Dispensable for in vitro Procoagulant Activity".

Kaufman et al, *Proteases in Biological Control and Biotechnol.,* J. Gen. Biochem. Supp., 10D 275 (1968).

*Primary Examiner*—Robin Teskin

*Attorney, Agent, or Firm*—David L. Berstein; Bruce M. Eisen; Ellen J. Kapinos

[57] ABSTRACT

Novel procoagulant proteins are disclosed which comprise the amino acid sequence:

A-X-B wherein region A represents the polypeptide sequence Ala-20 through Arg-759 substantially as shown in Table 1; region B represents the polypeptide sequence Ser-1709 through Tyr-2351 substantially as shown in Table 1; and region X represents a polypeptide sequence comprising up to 949 amino acids substantially duplicative of sequences of amino acids within the sequence SER-760 through Arg-1708 of Table 1, wherein the amino terminus of X is covalently bonded through a peptide bond designated "-" to the carboxy terminus of A, and the carboxy terminus of X is likewise bonded to the amino terminus of B. Methods of making such proteins and their use in pharmaceutical preparations is also disclosed.

12 Claims, No Drawings

NOVEL PROCOAGULANT PROTEINS

This application is a continuation in part of U.S. Ser. No. 725,350 (filed Apr. 12, 1985), now abandoned, the contents of which are hereby incorporated by reference.

This invention relates to a novel series of proteins which exhibit procoagulant properties. These proteins have marked structural differences from human factor VIII:C, but have similar procoagulant activity.

Factor VIII:C is the blood plasma protein that is defective or absent in Hemophilia A disease. This disease is a hereditary bleeding disorder affecting approximately one in 20,000 males. The structure of factor VIII:C is described in U.S. Patent Applications Ser. Nos. 546,650 filed Oct. 28, 1983 and 644,036 filed Aug. 24, 1984, which are incorporated herein by reference and in *Nature.* 312:306, 307, 326 and 342.

One of the problems presently encountered with the use of human factor VIII:C for treatment of hemophilia arises from its antigenicity. A significant percentage of hemophiliacs have developed an immune reaction to the factor VIII:C used for their treatment. Non-hemophiliacs can also develop or acquire hemophilia when their immune systems become sensitized to factor VIII:C and produce circulating antibodies or "inhibitors" to factor VIII:C. In either case, the effect is the neutralization of whatever factor VIII:C is present in the patient, making treatment very difficult. Until now, the method of choice for treating hemophiliacs with this problem has been to administer, in cases of severe bleeding episodes, non-human factor VIII:C, such as treated porcine factor VIII:C. See Kernoff et al., *Blood* 63:31 (1984). However, the antibodies which neutralize the clotting ability of human factor VIII:C will react to a varying extent with factor VIII:C of other species, and the porcine protein is itself antigenic, thus both the short-term and long-term effectiveness of such treatment will vary.

Additionally, patients frequently display adverse reactions to infusion with the porcine factor VIII:C. The use of porcine factor VIII:C in spite of the risks has been justified because of the lack of reliably effective alternatives. Kernoff, supra at 38. The present invention provides an alternative to the administration of porcine factor VIII:C.

This invention provides for proteins which have procoagulant activity similar to that of factor VIII:C and also have substantially lower molecular weight. These proteins are schematically depicted by formula (1) as follows:

$$A\text{-}X\text{-}B \qquad (1)$$

wherein A represents a polypeptide sequence substantially duplicative of the sequence Ala-20 through Arg-759; B represents a polypeptide sequence substantially duplicative of the sequence Ser-1709 through the C-terminal Tyr-2351; and X represents a polypeptide sequence of up to 949 amino acids substantially duplicative of sequences of amino acids within the sequence Ser-760 through Arg-1708. The amino terminus of region X is covalently bonded through a peptide bond (designated "-" in formula 1) to the carboxy terminus of A. The carboxy terminus of region X is likewise bonded to the amino terminus of B. Numbering of amino acids throughout this disclosure is with reference to the numbering of amino acids in Table 1 in which the first amino acid, Met, of the leader sequence is assigned Number 1. Protein domain X may comprise a continuous but shorter sequence selected from the region Ser-760 through Arg-1708. Alternatively X may comprise two or more amino acid sequences selected from that region which are covalently bonded by a peptide bond (maintaining an ascending numerical order of amino acids).

TABLE 1

5' GAATTCCCCACTGGGTAAGTTCCTTAAAGCTCTGGAAAGAAATTCCGACTTTTCATTAAATCAGAAATT

TTACTTTTTTCCCCTCCTGGGACCTAAAGATATTTAGAGAAGAATTAACCTTTTGCTTCTCCAGTTGAACATTTCTAGCAATAAGTC

| | | | | | | | | | | | | | | | | | | |
|---|---|---|---|---|---|---|---|---|---|---|---|---|---|---|---|---|---|---|
| MET | Gln | Ile | Glu | Leu | Ser | Thr | Cys | Phe | Phe | Leu | Cys | Leu | Leu | Arg | Phe | Cys | Phe | 18 |
| ATG | CAA | ATA | CAG | CTC | TCC | ACC | TGC | TTC | TTT | CTG | TGC | CTT | TTG | CCA | TTC | TCC | TTT | |
| Ser | Ala | Thr | Arg | Arg | Tyr | Tyr | Leu | Gly | Ala | Val | Glu | Leu | Ser | Trp | Asp | Tyr | MET | 36 |
| ACT | CCC | ACC | AGA | AGA | TAC | TAC | CTG | GGT | CCA | CTG | GAA | CTC | TCA | TGC | GAC | TAT | ATC | |
| Gln | Ser | Asp | Leu | Gly | Glu | Leu | Pro | Val | Asp | Ala | Arg | Phe | Pro | Pro | Arg | Val | Pro | 54 |
| CAA | AGT | GAT | CTC | GGT | CAG | CTG | CCT | GTG | CAC | GCA | AGA | TTT | CCT | CCT | AGA | CTG | CCA | |
| Lys | Ser | Phe | Pro | Phe | Asn | Thr | Ser | Val | Val | Tyr | Lys | Lys | Thr | Leu | Phe | Val | Glu | 72 |
| AAA | TCT | TTT | CCA | TTC | AAC | ACC | TCA | CTC | GTG | TAC | AAA | AAG | ACT | CTG | TTT | GTA | GAA | |
| Phe | Thr | Val | His | Leu | Phe | Asn | Ile | Ala | Lys | Pro | Arg | Pro | Pro | Trp | MET | Gly | Leu | 90 |
| TTC | ACG | GTT | CAC | CTT | TTC | AAC | ATC | CCT | AAG | CCA | ACC | CCA | CCC | TGG | ATG | CCT | CTG | |
| Leu | Gly | Pro | Thr | Ile | Gln | Ala | Glu | Val | Tyr | Asp | Thr | Val | Val | Ile | Thr | Leu | Lys | 108 |
| CTA | GGT | CCT | ACC | ATC | CAG | CCT | GAG | GTT | TAT | CAT | ACA | GTG | GTC | ATT | ACA | CTT | AAG | |
| Asn | MET | Ala | Ser | His | Pro | Val | Ser | Leu | His | Ala | Val | Gly | Val | Ser | Tyr | Trp | Lys | 126 |
| AAC | ATG | GCT | TCC | CAT | CCT | GTC | ACT | CTT | CAT | GCT | GTT | CGT | GTA | TCC | TAC | TGG | AAA | |
| Ala | Ser | Glu | Gly | Ala | Glu | Tyr | Asp | Asp | Gln | Thr | Ser | Gln | Arg | Glu | Lys | Glu | Asp | 144 |
| GCT | TCT | CAG | CCA | CCT | CAA | TAT | CAT | CAT | CAC | ACC | ACT | CAA | AGG | CAG | AAA | GAA | CAT | |
| Asp | Lys | Val | Phe | Pro | Gly | Gly | Ser | His | Thr | Tyr | Val | Trp | Gln | Val | Leu | Lys | Glu | 162 |
| GAT | AAA | GTC | TTC | CCT | CCT | GGA | ACC | CAT | ACA | TAT | CTC | TCC | CAG | CTC | CTG | AAA | GAG | |
| Asn | Gly | Pro | MET | Ala | Ser | Asp | Pro | Leu | cys | Leu | Thr | Tyr | Ser | Tyr | Leu | Ser | His | 180 |
| AAT | GGT | CCA | ATG | GCC | TCT | CAC | CCA | CTG | TCC | CTT | ACC | TAC | TCA | TAT | CTT | TCT | CAT | |
| Val | Asp | Leu | Val | Lys | Asp | Leu | Asn | Ser | Gly | Leu | Ile | Gly | Ala | Leu | Leu | Val | Cys | 198 |
| GTG | GAC | CTG | CTA | AAA | GAC | TTG | AAT | TCA | CGC | CTC | ATT | GGA | CCC | CTA | CTA | CTA | TGT | |
| Arg | Glu | Gly | Ser | Leu | Ala | Lys | Glu | Lys | Thr | Gln | Thr | Leu | His | Lys | Phe | Ile | Leu | 216 |
| AGA | CAA | GGG | AGT | CTG | GCC | AAG | CAA | AAG | ACA | CAG | ACC | TTG | CAC | AAA | TTT | ATA | CTA | |
| Leu | Phe | Ala | Val | Phe | Asp | Glu | Gly | Lys | Ser | Trp | His | Ser | Glu | Thr | Lys | Asn | Ser | 234 |
| CTT | TTT | GCT | GTA | TTT | CAT | GAA | GGG | AAA | ACT | TGC | CAC | TCA | GAA | ACA | AAG | AAC | TCC | |
| Leu | MET | Gln | Asp | Arg | Asp | Ala | Ala | Ser | Ala | Arg | Ala | Trp | Pro | Lys | MET | His | Thr | 252 |
| TTG | ATG | CAG | CAT | AGG | CAT | GCT | CCA | TCT | CCT | CCG | GCC | TGG | CCT | AAA | ATG | CAC | ACA | |
| Val | Asn | Gly | Tyr | Val | Asn | Arg | Ser | Leu | Pro | Gly | Leu | Ile | Gly | Cys | His | Arg | Lys | 270 |
| GTC | AAT | CGT | TAT | GTA | AAC | AGG | TCT | CTG | CCA | CCT | CTG | ATT | CCA | TCC | CAC | ACG | AAA | |
| Ser | Val | Tyr | Trp | His | Val | Ile | Gly | MET | Gly | Thr | Thr | Pro | Glu | Val | His | Ser | Ile | 288 |
| TCA | CTC | TAT | TGG | CAT | CTG | ATT | GCA | ATG | GGC | ACC | ACT | CCT | GAA | GTC | CAC | TCA | ATA | |
| Phe | Lue | Glu | Gly | His | Thr | Phe | leu | Val | Arg | Asn | His | Arg | Gln | Ala | Ser | Leu | Glu | 306 |
| TTC | CTC | CAA | CCT | CAC | ACA | TTT | CTT | CTC | ACC | AAC | CAT | CCC | CAC | CCG | TCC | TTG | CAA | |

TABLE 1-continued

| | | | | | | | | | | | | | | | | | | |
|---|---|---|---|---|---|---|---|---|---|---|---|---|---|---|---|---|---|---|
| Ile | Ser | Pro | Ile | Thr | Phe | Leu | Thr | Ala | Gln | Thr | Leu | Leu | MET | Asp | Leu | Gly | Gln | 324 |
| ATC | TCG | CCA | ATA | ACT | TTC | CTT | ACT | CCT | CAA | ACA | CTC | TTG | ATG | CAC | CTT | GGA | CAG | |
| Phe | Leu | Leu | Phe | Cys | His | Ile | Ser | Ser | His | Gln | His | Asp | Gly | MET | Glu | Ala | Tyr | 342 |
| TTT | CTA | CTG | TTT | TCT | CAT | ATC | TCT | TCC | CAC | CAA | CAT | GAT | GGC | ATG | CAA | GCT | TAT | |
| Val | Lys | Val | Asp | Ser | Cys | Pro | Glu | Glu | Pro | Gln | Leu | Arg | MET | Lys | Asn | Asn | Glu | 360 |
| GTC | AAA | GTA | GAC | AGC | TGT | CCA | GAG | GAA | CCC | CAA | CTA | CGA | ATG | AAA | AAT | AAT | GAA | |
| Glu | Ala | Glu | Asp | Tyr | Asp | Asp | Asp | Leu | Thr | Asp | Ser | Glu | MET | Asp | Val | Val | Arg | 378 |
| GAA | GCG | GAA | GAC | TAT | GAT | GAT | GAT | CTT | ACT | CAT | TCT | GAA | ATG | GAT | CTG | GTC | AGG | |
| Phe | Asp | Asp | Asp | Asn | Ser | Pro | Ser | Phe | Ile | Gln | Ile | Arg | Ser | Val | Ala | Lys | Lys | 396 |
| TTT | GAT | GAT | GAC | AAC | TCT | CCT | TCC | TTT | ATC | CAA | ATT | CCC | TCA | GTT | GCC | AAG | AAG | |
| His | Pro | Lys | Thr | Trp | Val | His | Tyr | Ile | Aln | Ala | Glu | Glu | Glu | Asp | Trp | Asp | Tyr | 414 |
| CAT | CCT | AAA | ACT | TGG | GTA | CAT | TAC | ATT | GCT | GCT | GAA | GAG | GAG | GAC | TGG | GAC | TAT | |
| Ala | Pro | Leu | Val | Leu | Ala | Pro | Asp | Asp | Arg | Ser | Tyr | Lys | Ser | Gln | Tyr | Leu | Asn | 432 |
| GCT | CCC | TTA | GTC | CTC | GCC | CCC | CAT | GAC | AGA | AGT | TAT | AAA | AGT | CAA | TAT | TTG | AAC | |
| Asn | Gly | Pro | Gln | Arg | Ile | Gly | Arg | Lyn | Tyr | Lys | Lys | Val | Arg | Phe | MET | Ala | Tyr | 450 |
| AAT | GCC | CCT | CAG | CGG | ATT | GGT | AGG | AAC | TAC | AAA | AAA | CTC | CGA | TTT | ATG | CCA | TAC | |
| Thr | Asp | Glu | Thr | Phe | Lys | Thr | Arg | Glu | Ala | Ile | Gln | His | Glu | Ser | Gly | Ile | Leu | 468 |
| ACA | CAT | GAA | ACC | TTT | AAG | ACT | CGT | GAA | CCT | ATT | CAG | CAT | GAA | TCA | CCA | ATC | TTG | |
| Gly | Pro | Leu | Leu | Tyr | Gly | Glu | Val | Gly | Asp | Thr | Leu | Leu | Ile | Ile | Phe | Lys | Asn | 486 |
| GGA | CCT | TTA | CTT | TAT | GGG | GAA | GTT | CCA | GAC | ACA | CTG | TTC | ATT | ATA | TTT | AAG | AAT | |
| Gln | Ala | Ser | Arg | Pro | Tyr | Asn | Ile | Tyr | Pro | His | Gly | Ile | Thr | Asp | Val | Arg | Pro | 504 |
| CAA | GCA | AGC | ACA | CCA | TAT | AAC | ATC | TAC | CCT | CAC | CGA | ATC | ACT | CAT | GTC | CGT | CCT | |
| Leu | Tyr | Ser | Arg | Arg | Leu | Pro | Lys | Gly | Val | Lys | His | Leu | Lys | Asp | Phe | Pro | Ile | 522 |
| TTG | TAT | TCA | AGG | AGA | TTA | CCA | AAA | GGT | GTA | AAA | CAT | TTG | AAG | GAT | TTT | CCA | ATT | |
| Leu | Pro | Gly | Glu | Ile | Phe | Lys | Tyr | Lys | Trp | Thr | Val | Thr | Val | Glu | Asp | Gly | Pro | 540 |
| CTG | CCA | GGA | GAA | ATA | TTC | AAA | TAT | AAA | TGG | ACA | GTG | ACT | GTA | CAA | CAT | GGG | CCA | |
| Thr | Lys | Ser | Asp | Pro | Arg | Cys | Leu | Thr | Arg | Tyr | Tyr | Ser | Ser | Phe | Val | Asn | MET | 558 |
| ACT | AAA | TCA | GAT | CCT | CGG | TGC | CTG | ACC | CGC | TAT | TAC | TCT | ACT | TTC | GTT | AAT | ATG | |
| Glu | Arg | Asp | Leu | Ala | Ser | Gly | Leu | Ile | Gly | Pro | Leu | Leu | Ile | Cys | Tyr | Lys | Glu | 576 |
| GAG | AGA | GAT | CTA | GCT | TCA | GGA | CTC | ATT | CGC | CCT | CTC | CTC | ATC | TGC | TAC | AAA | GAA | |
| Ser | Val | Asp | Gln | Arg | Gly | Asn | Gln | Ile | MET | Ser | Asp | Lys | Arg | Asn | Val | Ile | Leu | 594 |
| TCT | GTA | GAT | CAA | AGA | GGA | AAC | CAG | ATA | ATG | TCA | GAC | AAG | AGG | AAT | GTC | ATG | CTG | |
| Phe | Ser | Vnl | Phe | Asp | Glu | Asn | Arg | Ser | Trp | Tyr | Leu | Thr | Glu | Asp | Ile | Gln | Arg | 612 |
| TTT | TCT | GTA | TTT | CAT | CAG | AAC | CGA | AGC | TCG | TAC | CTC | ACA | CAG | AAT | ATA | CAA | CGC | |
| Phe | Leu | Pro | Asn | Pro | Ala | Gly | Val | Gln | Leu | Glu | Asp | Pro | Glu | Phe | Gln | Ala | Ser | 630 |
| TTT | CTC | CCC | AAT | CCA | CCT | CGA | GTG | CAG | CTT | CAG | CAT | CCA | GAG | TTC | CAA | GCC | TCC | |

TABLE 1-continued

| | | | | | | | | | | | | | | | | | | |
|---|---|---|---|---|---|---|---|---|---|---|---|---|---|---|---|---|---|---|
| Asn<br>AAC | Ile<br>ATC | MET<br>ATG | His<br>CAC | Ser<br>ACC | Ile<br>ATC | Asn<br>AAT | Gly<br>GGC | Tyr<br>TAT | Val<br>CTT | Phe<br>TTT | Asp<br>CAT | Ser<br>ACT | Leu<br>TTG | Gln<br>CAG | Leu<br>TTG | Ser<br>TCA | Val<br>GTT | 648 |
| Cys<br>TGT | Leu<br>TTG | His<br>CAT | Glu<br>CAG | Val<br>CTG | Ala<br>CCA | Tyr<br>TAC | Trp<br>TGG | Tyr<br>TAC | Ile<br>ATT | Leu<br>CTA | Ser<br>ACC | Ile<br>ATT | Gly<br>GGA | Ala<br>GCA | Gln<br>CAG | Thr<br>ACT | Asp<br>CAC | 666 |
| Phe<br>TTC | Leu<br>CTT | Ser<br>TCT | Val<br>GTC | Phe<br>TTC | Phe<br>TTC | Ser<br>TCT | Gly<br>GGA | Tyr<br>TAT | Thr<br>ACC | Phe<br>TTC | Lys<br>AAA | His<br>CAC | Lys<br>AAA | MET<br>ATG | Val<br>GTC | Tyr<br>TAT | Glu<br>CAA | 684 |
| Asp<br>GAC | Thr<br>ACA | Leu<br>CTC | Thr<br>ACC | Leu<br>CTA | Phe<br>TTC | Pro<br>CCA | Phe<br>TTC | Ser<br>TCA | Gly<br>GGA | Glu<br>CAA | Thr<br>ACT | Val<br>GTC | Phe<br>TTC | MET<br>ATG | Ser<br>TCG | MET<br>ATG | Glu<br>GAA | 702 |
| Asn<br>AAC | Pro<br>CCA | Gly<br>GGT | Leu<br>CTA | Trp<br>TGG | Ile<br>ATT | Leu<br>CTG | Gly<br>GGG | Cys<br>TGC | His<br>CAC | Asn<br>AAC | Ser<br>TCA | Asp<br>GAC | Phe<br>TTT | Arg<br>CGG | Asn<br>AAC | Arg<br>AGA | Gly<br>CCC | 720 |
| MET<br>ATG | Thr<br>ACC | Ala<br>CCC | Leu<br>TTA | Leu<br>CTG | Lys<br>AAG | Val<br>GTT | Ser<br>TCT | Ser<br>AGT | Cys<br>TGT | Asp<br>GAC | Lys<br>AAG | Asn<br>AAC | Thr<br>ACT | Gly<br>GGT | Asp<br>GAT | Tyr<br>TAT | Tyr<br>TAC | 738 |
| Glu<br>GAG | Asp<br>GAC | Ser<br>ACT | Tyr<br>TAT | Glu<br>GAA | Asp<br>CAT | Ile<br>ATT | Ser<br>TCA | Ala<br>GCA | Tyr<br>TAC | Leu<br>TTG | Leu<br>CTG | Ser<br>ACT | Lys<br>AAA | Asn<br>AAC | Asn<br>AAT | Ala<br>GCC | Ile<br>ATT | 756 |
| Glu<br>GAA | Pro<br>CCA | Arg<br>AGA | Ser<br>ACC | Phe<br>TTC | Ser<br>TCC | Gln<br>CAG | Asn<br>AAT | Ser<br>TCA | Arg<br>AGA | His<br>CAC | Pro<br>CCT | Ser<br>AGC | Thr<br>ACT | Arg<br>AGG | Gln<br>CAA | Lys<br>AAG | Gln<br>CAA | 774 |
| Phe<br>TTT | Asn<br>AAT | Ala<br>GCC | Thr<br>ACC | Thr<br>ACA | Ile<br>ATT | Pro<br>CCA | Glu<br>CAA | Asn<br>AAT | Asp<br>GAC | Ile<br>ATA | Glu<br>CAG | Lys<br>AAG | Thr<br>ACT | Asp<br>CAC | Pro<br>CCT | Trp<br>TGG | Phe<br>TTT | 792 |
| Ala<br>GCA | His<br>CAC | Arg<br>AGA | Thr<br>ACA | Pro<br>CCT | MET<br>ATG | Pro<br>CCT | Lys<br>AAA | Ile<br>ATA | Gln<br>CAA | Asn<br>AAT | Val<br>GTC | Ser<br>TCC | Ser<br>TCT | Ser<br>ACT | Asp<br>GAT | Leu<br>TTG | Leu<br>TTG | 810 |
| MET<br>ATG | Leu<br>CTC | Leu<br>TTG | Arg<br>CGA | Gln<br>CAG | Ser<br>ACT | Pro<br>CCT | Thr<br>ACT | Pro<br>CCA | His<br>CAT | Gly<br>GGG | Leu<br>CTA | Ser<br>TCC | Leu<br>TTA | Ser<br>TCT | Asp<br>GAT | Leu<br>CTC | Gln<br>CAA | 828 |
| Glu<br>GAA | Ala<br>GCC | Lys<br>AAA | Tyr<br>TAT | Glu<br>GAG | Thr<br>ACT | Phe<br>TTT | Ser<br>TCT | Asp<br>GAT | Asp<br>GAT | Pro<br>CCA | Ser<br>TCA | Pro<br>CCT | Gly<br>GGA | Ala<br>GCA | Ile<br>ATA | Asp<br>CAC | Ser<br>ACT | 846 |
| Asn<br>AAT | Asn<br>AAC | Ser<br>AGC | Leu<br>CTG | Ser<br>TCT | Glu<br>GAA | MET<br>ATG | Thr<br>ACA | His<br>CAC | Phe<br>TTC | Arg<br>ACC | Pro<br>CCA | Gln<br>CAG | Leu<br>CTC | His<br>CAT | His<br>CAC | Ser<br>ACT | Gly<br>GGG | 864 |
| Asp<br>GAC | MET<br>ATG | Val<br>GTA | Phe<br>TTT | Thr<br>ACC | Pro<br>CCT | Glu<br>GAG | Ser<br>TCA | Gly<br>GGC | Leu<br>CTC | Gln<br>CAA | Leu<br>TTA | Arg<br>AGA | Leu<br>TTA | Asn<br>AAT | Glu<br>CAG | Lys<br>AAA | Leu<br>CTG | 882 |
| Gly<br>GGG | Thr<br>ACA | Thr<br>ACT | Ala<br>GCA | Ala<br>GCA | Thr<br>ACA | Glu<br>GAG | Leu<br>TTC | Lys<br>AAG | Lys<br>AAA | Leu<br>CTT | Asp<br>CAT | Phe<br>TTC | Lys<br>AAA | Val<br>CTT | Ser<br>TCT | Ser<br>ACT | Thr<br>ACA | 900 |
| Ser<br>TCA | Asn<br>AAT | Asn<br>AAT | Leu<br>CTG | Ile<br>ATT | Ser<br>TCA | Thr<br>ACA | Ile<br>ATT | Pro<br>CCA | Ser<br>TCA | Asp<br>GAC | Asn<br>AAT | Leu<br>TTG | Ala<br>GCA | Ala<br>GCA | Gly<br>CCT | Thr<br>ACT | Asp<br>CAT | 918 |
| Asn<br>AAT | Thr<br>ACA | Ser<br>AGT | Ser<br>TCC | Leu<br>TTA | Gly<br>GGA | Pro<br>CCC | Pro<br>CCA | Ser<br>ACT | MET<br>ATG | Pro<br>CCA | Val<br>GTT | His<br>CAT | Tyr<br>TAT | Asp<br>CAT | Ser<br>ACT | Gln<br>CAA | Leu<br>TTA | 936 |
| Asp | Thr | Thr | Leu | Phe | Gly | Lys | Lys | Ser | Ser | Pro | Leu | Thr | Glu | Ser | Gly | Gly | Pro | 954 |

TABLE 1-continued

| CAT | ACC | ACT | CTA | TTT | GGC | AAA | AAG | TCA | TCT | CCC | CTT | ACT | GAG | TCT | GGT | GCA | CCT | |
|---|---|---|---|---|---|---|---|---|---|---|---|---|---|---|---|---|---|---|
| Leu<br>CTG | Ser<br>AGC | Leu<br>TTG | Ser<br>ACT | Glu<br>CAA | Glu<br>CAA | Asn<br>AAT | Asn<br>AAT | Asp<br>CAT | Ser<br>TCA | Lys<br>AAG | Leu<br>TTG | Leu<br>TTA | Glu<br>CAA | Ser<br>TCA | Gly<br>CCT | Leu<br>TTA | MET<br>ATC | 972 |
| Asn<br>AAT | Ser<br>ACC | Gln<br>CAA | Glu<br>CAA | Ser<br>ACT | Ser<br>TCA | Trp<br>TGG | Gly<br>CGA | Lys<br>AAA | Asn<br>AAT | Val<br>CTA | Ser<br>TCG | Ser<br>TCA | Thr<br>ACA | Glu<br>CAG | Ser<br>ACT | Gly<br>CGT | Arg<br>ACC | 990 |
| Leu<br>TTA | Phe<br>TTT | Lys<br>AAA | Gly<br>CGG | Lys<br>AAA | Arg<br>AGA | Ala<br>GCT | His<br>CAT | Gly<br>GCA | Pro<br>CCT | Ala<br>CCT | Leu<br>TTG | Leu<br>TTG | Thr<br>ACT | Lys<br>AAA | Asp<br>CAT | Asn<br>AAT | Ala<br>GCC | 1,008 |
| Leu<br>TTA | Phe<br>TTC | Lys<br>AAA | Val<br>GTT | Ser<br>AGC | Ile<br>ATC | Ser<br>TCT | Leu<br>TTG | Leu<br>TTA | Lys<br>AAG | Thr<br>ACA | Asn<br>AAC | Lys<br>AAA | Thr<br>ACT | Ser<br>TCC | Asn<br>AAT | Asn<br>AAT | Ser<br>TCA | 1,026 |
| Ala<br>CCA | Thr<br>ACT | Asn<br>AAT | Arg<br>ACA | Lys<br>AAG | Thr<br>ACT | His<br>CAC | Ile<br>ATT | Asp<br>CAT | Gly<br>CGC | Pro<br>CCA | Ser<br>TCA | Leu<br>TTA | Leu<br>TTA | Ile<br>ATT | Glu<br>GAG | Asn<br>AAT | Ser<br>AGT | 1,044 |
| Pro<br>CCA | Ser<br>TCA | Val<br>GTC | Trp<br>TGG | Gln<br>CAA | Asn<br>AAT | Ile<br>ATA | Leu<br>TTA | Glu<br>GAA | Ser<br>AGT | Asp<br>GAC | Thr<br>ACT | Glu<br>CAG | Phe<br>TTT | Lys<br>AAA | Lys<br>AAA | Val<br>GTG | Thr<br>ACA | 1,062 |
| Pro<br>CCT | Leu<br>TTG | Ile<br>ATT | His<br>CAT | Asp<br>GAC | Arg<br>AGA | MET<br>ATG | Leu<br>CTT | MET<br>ATG | Asp<br>GAC | Lys<br>AAA | Asn<br>AAT | Ala<br>GCT | Thr<br>ACA | Ala<br>CCT | Leu<br>TTC | Arg<br>AGG | Leu<br>CTA | 1,080 |
| Asn<br>AAT | His<br>CAT | MET<br>ATG | Ser<br>TCA | Asn<br>AAT | Lys<br>AAA | Thr<br>ACT | Thr<br>ACT | Ser<br>TCA | Ser<br>TCA | Lys<br>AAA | Asn<br>ACC | MET<br>ATG | Glu<br>GAA | MET<br>ATG | Val<br>CTC | Gln<br>CAA | Gln<br>CAG | 1,098 |
| Lys<br>AAA | Lys<br>AAA | Glu<br>GAG | Gly<br>GGC | Pro<br>CCC | Ile<br>ATT | Pro<br>CCA | Pro<br>CCA | Asp<br>GAT | Ala<br>CCA | Gln<br>CAA | Asn<br>AAT | Pro<br>CCA | Asp<br>GAT | MET<br>ATG | Ser<br>TCG | Phe<br>TTC | Phe<br>TTT | 1,116 |
| Lys<br>AAG | MET<br>ATG | Leu<br>CTA | Phe<br>TTC | Leu<br>TTG | Pro<br>CCA | Glu<br>GAA | Ser<br>TCA | Ala<br>CCA | Arg<br>ACC | Trp<br>TGG | Ile<br>ATA | Gln<br>CAA | Arg<br>AGG | Thr<br>ACT | His<br>CAT | Gly<br>GCA | Lys<br>AAG | 1,134 |
| Asn<br>AAC | Ser<br>TCT | Leu<br>CTG | Asn<br>AAC | Ser<br>TCT | Gly<br>GGG | Gln<br>CAA | Gly<br>GGC | Pro<br>CCC | Ser<br>ACT | Pro<br>CCA | Lys<br>AAC | Gln<br>CAA | Leu<br>TTA | Val<br>GTA | Ser<br>TCC | Leu<br>TTA | Gly<br>GCA | 1,152 |
| Pro<br>CCA | Glu<br>GAA | Lys<br>AAA | Ser<br>TCT | Val<br>GTG | Glu<br>GAA | Gly<br>GGT | Gln<br>CAG | Asn<br>AAT | Phe<br>TTC | Leu<br>TTG | Ser<br>TCT | Glu<br>GAG | Lys<br>AAA | Asn<br>AAC | Lys<br>AAA | Val<br>GTG | Val<br>GTA | 1,170 |
| Val<br>GTA | Gly<br>GGA | Lys<br>AAG | Gly<br>GGT | Gly<br>GAA | Phe<br>TTT | Thr<br>ACA | Lys<br>AAG | Asp<br>CAC | Val<br>GTA | Gly<br>CGA | Leu<br>CTC | Lys<br>AAA | Glu<br>GAG | MET<br>ATG | Val<br>CTT | Phe<br>TTT | Pro<br>CCA | 1,188 |
| Ser<br>AGC | Ser<br>AGC | Arg<br>ACA | Asn<br>AAC | Leu<br>CTA | Phe<br>TTT | Leu<br>CTT | Thr<br>ACT | Asn<br>AAC | Leu<br>TTG | Asp<br>GAT | Asn<br>AAT | Leu<br>TTA | His<br>CAT | Glu<br>GAA | Asn<br>AAT | Asn<br>AAT | Thr<br>ACA | 1,206 |
| His<br>CAC | Asn<br>AAT | Gln<br>CAA | Glu<br>CAA | Lys<br>AAA | Lys<br>AAA | Ile<br>ATT | Gln<br>CAG | Glu<br>CAA | Glu<br>CAA | Ile<br>ATA | Glu<br>GAA | Lys<br>AAG | Lys<br>AAG | Glu<br>GAA | Thr<br>ACA | Leu<br>TTA | Ile<br>ATC | 1,224 |
| Gln<br>CAA | Glu<br>GAG | Asn<br>AAT | Val<br>GTA | Val<br>GTT | Leu<br>TTG | Pro<br>CCT | Gln<br>CAG | Ile<br>ATA | His<br>CAT | Thr<br>ACA | Val<br>CTG | Thr<br>ACT | Gly<br>GGC | Thr<br>ACT | Lys<br>AAG | Asn<br>AAT | Phe<br>TTC | 1,242 |
| MET<br>ATG | Lys<br>AAC | Asn<br>AAC | Leu<br>CTT | Phe<br>TTC | Leu<br>TAA | Leu<br>CTG | Ser<br>ACC | Thr<br>ACT | Arg<br>AGG | Gln<br>GAA | Asn<br>AAT | Val<br>GTA | Glu<br>GAA | Gly<br>GGT | Ser<br>TCA | Tyr<br>TAT | Glu<br>GAG | 1,260 |

TABLE 1-continued

| | | | | | | | | | | | | | | | | | | |
|---|---|---|---|---|---|---|---|---|---|---|---|---|---|---|---|---|---|---|
| Gly<br>GGG | Ala<br>GCA | Tyr<br>TAT | Ala<br>CCT | Pro<br>CCA | Val<br>GTA | Leu<br>CTT | Gln<br>CAA | Asp<br>CAT | Phe<br>TTT | Arg<br>AGG | Ser<br>TCA | Leu<br>TTA | Asn<br>AAT | Asp<br>GAT | Ser<br>TCA | Thr<br>ACA | Asn<br>AAT | 1,278 |
| Arg<br>AGA | Thr<br>ACA | Lys<br>AAG | Lys<br>AAA | His<br>CAC | Thr<br>ACA | Ala<br>CCT | His<br>CAT | Phe<br>TTC | Ser<br>TCA | Lys<br>AAA | Lys<br>AAA | Gly<br>CGG | Glu<br>CAG | Glu<br>CAA | Glu<br>CAA | Asn<br>AAC | Leu<br>TTG | 1,296 |
| Glu<br>CAA | Gly<br>GGC | Leu<br>TTG | Gly<br>GGA | Asn<br>AAT | Gln<br>CAA | Thr<br>ACC | Lys<br>AAG | Gln<br>CAA | Ile<br>ATT | Val<br>CTA | Glu<br>CAG | Lys<br>AAA | Tyr<br>TAT | Ala<br>CCA | Cys<br>TGC | Thr<br>ACC | Thr<br>ACA | 1,314 |
| Arg<br>AGC | Ile<br>ATA | Ser<br>TCT | Pro<br>CCT | Asn<br>AAT | Thr<br>ACA | Ser<br>AGC | Gln<br>CAG | Gln<br>CAG | Asn<br>AAT | Phe<br>TTT | Val<br>CTC | Thr<br>ACG | Gln<br>CAA | Arg<br>CCT | Ser<br>ACT | Lys<br>AAG | Arg<br>AGA | 1,332 |
| Ala<br>CCT | Leu<br>TTG | Lys<br>AAA | Gln<br>CAA | Phe<br>TTC | Arg<br>AGA | Leu<br>CTC | Pro<br>CCA | Leu<br>CTA | Glu<br>GAA | Glu<br>GAA | Thr<br>ACA | Glu<br>CAA | Leu<br>CTT | Glu<br>GAA | Lys<br>AAA | Arg<br>AGG | Ile<br>ATA | 1,350 |
| Ile<br>ATT | Val<br>GTG | Asp<br>GAT | Asp<br>GAC | Thr<br>ACC | Ser<br>TCA | Thr<br>ACC | Gln<br>CAC | Trp<br>TGG | Ser<br>TCC | Lys<br>AAA | Asn<br>AAC | MET<br>ATG | Lys<br>AAA | His<br>CAT | Leu<br>TTC | Thr<br>ACC | Pro<br>CCG | 1,368 |
| Ser<br>AGC | Thr<br>ACC | Leu<br>CTC | Thr<br>ACA | Gln<br>CAG | Ile<br>ATA | Asp<br>GAC | Tyr<br>TAC | Asn<br>AAT | Glu<br>GAG | Lys<br>AAG | Glu<br>GAC | Lys<br>AAA | Gly<br>GGG | Alu<br>GCC | Ile<br>ATT | Thr<br>ACT | Cln<br>CAG | 1,386 |
| Ser<br>TCT | Pro<br>CCC | Leu<br>TTA | Ser<br>TCA | Asp<br>GAT | Cys<br>TGC | Leu<br>CTT | Thr<br>ACG | Arg<br>AGG | Ser<br>ACT | His<br>CAT | Ser<br>AGC | Ile<br>ATC | Pro<br>CCT | Gln<br>CAA | Ala<br>GCA | Asn<br>AAT | Arg<br>AGA | 1,404 |
| Ser<br>TCT | Pro<br>CCA | Leu<br>TTA | Pro<br>CCC | Ile<br>ATT | Ala<br>GCA | Lys<br>AAG | Val<br>GTA | Ser<br>TCA | Ser<br>TCA | Phe<br>TTT | Pro<br>CCA | Ser<br>TCT | Ile<br>ATT | Arg<br>AGA | Pro<br>CCT | Ile<br>ATA | Tyr<br>TAT | 1,422 |
| Leu<br>CTG | Thr<br>ACC | Arg<br>AGG | Val<br>GTC | Leu<br>CTA | Phe<br>TTC | Gln<br>CAA | Asp<br>GAC | Asn<br>AAC | Ser<br>TCT | Ser<br>TCT | His<br>CAT | Leu<br>CTT | Pro<br>CCA | Ala<br>GCA | Ala<br>GCA | Ser<br>TCT | Tyr<br>TAT | 1,440 |
| Arg<br>ACA | Lys<br>AAG | Lys<br>AAA | Asp<br>GAT | Ser<br>TCT | Gly<br>GGG | Val<br>GTC | Gln<br>CAA | Glu<br>GAA | Ser<br>AGC | Ser<br>ACT | His<br>CAT | Phe<br>TTC | Leu<br>TTA | Gln<br>CAA | Gly<br>CGA | Ala<br>CCC | Lys<br>AAA | 1,458 |
| Lys<br>AAA | Asn<br>AAT | Asn<br>AAC | Leu<br>CTT | Ser<br>TCT | Leu<br>TTA | Ala<br>GCC | Ile<br>ATT | Leu<br>CTA | Thr<br>ACC | Leu<br>TTG | Glu<br>GAG | MET<br>ATG | Thr<br>ACT | Gly<br>CGT | Asp<br>CAT | Gln<br>CAA | Arg<br>AGA | 1,476 |
| Glu<br>GAG | Val<br>GTT | Gly<br>GGC | Ser<br>TCC | Leu<br>CTG | Gly<br>GGG | Thr<br>ACA | Ser<br>ACT | Ala<br>GCC | Thr<br>ACA | Asn<br>AAT | Ser<br>TCA | Val<br>GTC | Thr<br>ACA | Tyr<br>TAC | Lys<br>AAC | Lys<br>AAA | Val<br>GTT | 1,494 |
| Glu<br>CAG | Asn<br>AAC | Thr<br>ACT | Val<br>GTT | Leu<br>CTC | Pro<br>CCG | Lys<br>AAA | Pro<br>CCA | Asp<br>GAC | Leu<br>TTG | Pro<br>CCC | Lys<br>AAA | Thr<br>ACA | Ser<br>TCT | Gly<br>CGC | Lys<br>AAA | Val<br>CTT | Glu<br>GAA | 1,512 |
| Leu<br>TTG | Leu<br>CTT | Pro<br>CCA | Lys<br>AAA | Val<br>GTT | His<br>CAC | Ile<br>ATT | Tyr<br>TAT | Gln<br>CAG | Lys<br>AAG | Asp<br>CAC | Leu<br>CTA | Phe<br>TTC | Pro<br>CCT | Thr<br>ACG | Glu<br>GAA | Thr<br>ACT | Ser<br>AGC | 1,530 |
| Asn<br>AAT | Gly<br>CCG | Ser<br>TCT | Pro<br>CCT | Gly<br>GGC | His<br>CAT | Leu<br>CTG | Asp<br>GAT | Leu<br>CTC | Val<br>GTG | Glu<br>CAA | Gly<br>GGG | Ser<br>AGC | Leu<br>CTT | Leu<br>CTT | Gln<br>CAG | Gly<br>CGA | Thr<br>ACA | 1,548 |
| Glu<br>GAG | Gly<br>GGA | Ala<br>GCG | Ile<br>ATT | Lys<br>AAC | Trp<br>TGG | Asn<br>AAT | Glu<br>GAA | Ala<br>CCA | Asn<br>AAC | Arg<br>AGA | Pro<br>CCT | Gly<br>CGA | Lys<br>AAA | Val<br>CTT | Pro<br>CCC | Phe<br>TTT | Leu<br>CTG | 1,566 |
| Arg<br>AGA | Val<br>GTA | Ala<br>GCA | Thr<br>ACA | Glu<br>GAA | Ser<br>AGC | Ser<br>TCT | Ala<br>GCA | Lys<br>AAG | Thr<br>ACT | Pro<br>CCC | Ser<br>TCC | Lys<br>AAC | Leu<br>CTA | Leu<br>TTG | Asp<br>CAT | Pro<br>CCT | Leu<br>CTT | 1,584 |

TABLE 1-continued

| | | | | | | | | | | | | | | | | | | |
|---|---|---|---|---|---|---|---|---|---|---|---|---|---|---|---|---|---|---|
| Ala<br>GCT | Trp<br>TGG | Asp<br>GAT | Asn<br>AAC | His<br>CAC | Tyr<br>TAT | Gly<br>GGT | Thr<br>ACT | Gln<br>CAG | Ile<br>ATA | Pro<br>CCA | Lys<br>AAA | Glu<br>GAA | Glu<br>GAG | Trp<br>TGG | Lys<br>AAA | Ser<br>TCC | Gln<br>CAA | 1,602 |
| Glu<br>GAG | Lys<br>AAG | Ser<br>TCA | Pro<br>CCA | Glu<br>GAA | Lys<br>AAA | Thr<br>ACA | Ala<br>GCT | Phe<br>TTT | Lys<br>AAG | Lys<br>AAA | Lys<br>AAG | Asp<br>GAT | Thr<br>ACC | Ile<br>ATT | Leu<br>TTG | Ser<br>TCC | Leu<br>CTG | 1,520 |
| Asn<br>AAC | Ala<br>GCT | Cys<br>TGT | Glu<br>GAA | Ser<br>AGC | Asn<br>AAT | His<br>CAT | Ala<br>GCA | Ile<br>ATA | Ala<br>GCA | Ala<br>CCA | Ile<br>ATA | Asn<br>AAT | Glu<br>GAG | Gly<br>CGA | Gln<br>CAA | Asn<br>AAT | Lys<br>AAG | 1,638 |
| Pro<br>CCC | Glu<br>GAA | Ile<br>ATA | Glu<br>GAA | Val<br>GTC | Thr<br>ACC | Trp<br>TCC | Ala<br>GCA | Lys<br>AAG | Gln<br>CAA | Gly<br>CGT | Arg<br>AGG | Thr<br>ACT | Glu<br>CAA | Arg<br>AGG | Leu<br>CTC | Cys<br>TCC | Ser<br>TCT | 1,656 |
| Gln<br>CAA | Asn<br>AAC | Pro<br>CCA | Pro<br>CCA | Vnl<br>CTC | Leu<br>TTC | Lys<br>AAA | Arg<br>CCC | His<br>CAT | Gln<br>CAA | Arg<br>CGC | Glu<br>CAA | Ile<br>ATA | Thr<br>ACT | Arg<br>CGT | Thr<br>ACT | Thr<br>ACT | Leu<br>CTT | 1,674 |
| Gln<br>CAG | Ser<br>TCA | Asp<br>GAT | Gln<br>CAA | Glu<br>GAG | Glu<br>GAA | Ile<br>ATT | Asp<br>CAC | Tyr<br>TAT | Asp<br>CAT | Asp<br>CAT | Thr<br>ACC | Ile<br>ATA | Ser<br>TCA | Val<br>GTT | Glu<br>GAA | MET<br>ATG | Lys<br>AAG | 1,692 |
| Lys<br>AAG | Glu<br>GAA | Asp<br>GAT | The<br>TTT | Asp<br>GAC | Ile<br>ATT | Tyr<br>TAT | Asp<br>CAT | Glu<br>GAG | Asp<br>CAT | Glu<br>GAA | Asn<br>AAT | Gln<br>CAC | Ser<br>AGC | Pro<br>CCC | Arg<br>CGC | Ser<br>AGC | Phe<br>TTT | 1,710 |
| Gln<br>CAA | Lys<br>AAG | Lys<br>AAA | Thr<br>ACA | Arg<br>CCA | His<br>CAC | Tyr<br>TAT | Phe<br>TTT | Ile<br>ATT | Ala<br>GCT | Ala<br>GCA | Val<br>GTG | Glu<br>GAG | Arg<br>AGC | Leu<br>CTC | Trp<br>TGG | Asp<br>GAT | Tyr<br>TAT | 1,728 |
| Gly<br>CCG | MET<br>ATG | Ser<br>AGT | Ser<br>AGC | Ser<br>TCC | Pro<br>CCA | His<br>CAT | Val<br>GTT | Leu<br>CTA | Arg<br>AGA | Asn<br>AAC | Arg<br>AGG | Ala<br>GCT | Gln<br>CAG | Ser<br>AGT | Gly<br>GGC | Ser<br>ACT | Val<br>GTC | 1,746 |
| Pro<br>CCT | Gln<br>CAG | Phe<br>TTC | Lys<br>AAG | Lys<br>AAA | Val<br>GTT | Val<br>GTT | Phe<br>TTC | Gln<br>CAG | Glu<br>CAA | Phe<br>TTT | Thr<br>ACT | Asp<br>GAT | Gly<br>CGC | Ser<br>TCC | Phe<br>TTT | Thr<br>ACT | Gln<br>CAG | 1,764 |
| Pro<br>CCC | Leu<br>TTA | Tyr<br>TAC | Arg<br>CCT | Gly<br>GGA | Glu<br>GAA | Leu<br>CTA | Asn<br>AAT | Glu<br>GAA | His<br>CAT | Leu<br>TTG | Gly<br>GGA | Leu<br>CTC | Leu<br>CTG | Gly<br>GGG | Pro<br>CCA | Tyr<br>TAT | Ile<br>ATA | 1,782 |
| Arg<br>AGA | Ala<br>GCA | Glu<br>GAA | Val<br>GTT | Glu<br>GAA | Asp<br>GAT | Asn<br>AAT | Ile<br>ATC | MET<br>ATG | Val<br>GTA | Thr<br>ACT | Phe<br>TTC | Arg<br>AGA | Asn<br>AAT | Gln<br>CAG | Ala<br>GCC | Ser<br>TCT | Arg<br>CGT | 1,800 |
| Pro<br>CCC | Tyr<br>TAT | Ser<br>TCC | Phe<br>TTC | Tyr<br>TAT | Ser<br>TCT | Ser<br>AGC | Leu<br>CTT | Ile<br>ATT | Ser<br>TCT | Tyr<br>TAT | Glu<br>GAG | Glu<br>GAA | Asp<br>GAT | Gln<br>CAG | Arg<br>AGG | Gln<br>CAA | Gly<br>GGA | 1,818 |
| Ala<br>GCA | Glu<br>GAA | Pro<br>CCT | Arg<br>AGA | Lys<br>AAA | Asn<br>AAC | Phe<br>TTT | Val<br>GTC | Lys<br>AAG | Pro<br>CCT | Asn<br>AAT | Glu<br>GAA | Thr<br>ACC | Lys<br>AAA | Thr<br>ACT | Tyr<br>TAC | Phe<br>TTT | Trp<br>TGG | 1,836 |
| Lys<br>AAA | Val<br>CTG | Gln<br>CAA | His<br>CAT | His<br>CAT | MET<br>ATG | Ala<br>GCA | Pro<br>CCC | Thr<br>ACT | Lys<br>AAA | Asp<br>GAT | Glu<br>GAG | Phe<br>TTT | Asp<br>GAC | Cys<br>TGC | Lys<br>AAA | Ala<br>GCC | Trp<br>TGG | 1,854 |
| Ala<br>GCT | Tyr<br>TAT | Phe<br>TTC | Ser<br>TCT | Asp<br>GAT | Val<br>GTT | Asp<br>GAC | Leu<br>CTG | Glu<br>GAA | Lys<br>AAA | Asp<br>CAT | Val<br>GTG | His<br>CAC | Ser<br>TCA | Gly<br>GGC | Leu<br>CTG | Ile<br>ATT | Gly<br>GGA | 1,872 |
| Pro<br>CCC | Leu<br>CTT | Leu<br>CTG | Val<br>CTC | Cys<br>TGC | His<br>CAC | Thr<br>ACT | Asn<br>AAC | Thr<br>ACA | Leu<br>CTG | Asn<br>AAC | Pro<br>CCT | Ala<br>GCT | His<br>CAT | Gly<br>CCG | Arg<br>AGA | Gln<br>CAA | Val<br>CTG | 1,890 |
| Thr | Val | Glu | Glu | Phe | Ala | Leu | Phe | Phe | Thr | Ile | Phe | Asp | Glu | Thr | Lys | Ser | Trp | 1,908 |

TABLE 1-continued

| ACA | CTA | CAG | GAA | TTT | GCT | CTG | TTT | TTC | ACC | ATC | TTT | CAT | GAG | ACC | AAA | AGC | TCG | |
|---|---|---|---|---|---|---|---|---|---|---|---|---|---|---|---|---|---|---|
| Thy TAC | Phe TTC | Thr ACT | Glu CAA | Asn AAT | MET ATG | Glu CAA | Arg AGA | Asn AAC | Cys TGC | Arg ACC | Ala CCT | Pro CCC | Cys TGC | Asn AAT | Ile ATC | Gln CAG | MET ATG | 1,926 |
| Glu CAA | Asp GAT | Pro CCC | Thr ACT | Phe TTT | Lys AAA | Glu CAG | Asn AAT | Thr TAT | Arg CGC | Phe TTC | His CAT | Ala GCA | Ile ATC | Asn AAT | Gly CGC | Tyr TAC | Ile ATA | 1,944 |
| MET ATG | Asp CAT | Thr ACA | Leu CTA | Pro CCT | Gly GGC | Leu TTA | Val GTA | MET ATG | Ala GCT | Gln CAG | Asp GAT | Gln CAA | Arg AGG | Ile ATT | Arg CGA | Trp TCG | Tyr TAT | 1,962 |
| Leu CTC | Leu CTC | Ser AGC | MET ATG | Gly CGC | Ser AGC | Asn AAT | Glu CAA | Asn AAC | Ile ATC | His CAT | Ser TCT | Ile ATT | His CAT | Phe TTC | Ser ACT | Gly CCA | His CAT | 1,980 |
| Val GTG | Phe TTC | Thr ACT | Val CTA | Arg CCA | Lys AAA | Lys AAA | Glu CAG | Glu GAG | Tyr TAT | Lys AAA | MET ATG | Ala GCA | Leu CTG | Tyr TAC | Asn AAT | Leu CTC | Tyr TAT | 1,998 |
| Pro CCA | Gly CGT | Val GTT | Phe TTT | Glu GAC | Thr ACA | Val GTG | Glu GAA | MET ATG | Leu TTA | Pro CCA | Ser TCC | Lys AAA | Ala GCT | Gly GGA | Ile ATT | Trp TCC | Arg CGG | 2,016 |
| Val GTG | Glu GAA | Cys TGC | Leu CTT | Ile ATT | Gly CCC | Glu GAC | His CAT | Leu CTA | His CAT | Ala CCT | Gly CGG | MET ATG | Ser AGC | Thr ACA | Leu CTT | Phe TTT | Leu CTG | 2,034 |
| Val GTG | Tyr TAC | Ser AGC | Asn AAT | Lys AAG | Cys TGT | Glu CAG | Thr ACT | Pro CCC | Leu CTG | Gly GGA | MET ATG | Ala GCT | Ser TCT | Gly GGA | His CAC | Ile ATT | Arg AGA | 2,052 |
| Asp CAT | Phe TTT | Gln CAG | Ile ATT | Thr ACA | Ala GCT | Ser TCA | Gly CGA | Gln CAA | Tyr TAT | Gly GCA | Gln CAG | Trp TGG | Ala GCC | Pro CCA | Lys AAG | Leu CTG | Ala GCC | 2,070 |
| Arg AGA | Leu CTT | His CAT | Tyr TAT | Ser TCC | Gly GGA | Ser TCA | Ile ATC | Asn AAT | Ala GCC | Trp TGG | Set AGC | Thr ACC | Lys AAG | Glu GAG | Pro CCC | Phe TTT | Ser TCT | 2,088 |
| Trp TGC | Ile ATC | Lys AAG | Val GTG | Asp CAT | Leu CTG | Leu TTG | Ala GCA | Pro CCA | MET ATG | Ile ATT | Ile ATT | His CAC | Gly GGC | Ile ATC | Lys AAG | Thr ACC | Gln CAG | 2,106 |
| Gly GGT | Ala GCC | Arg CGT | Gln CAG | Lys AAG | Phe TTC | Ser TCC | Ser AGC | Leu CTC | Tyr TAC | Ile ATC | Ser TCT | Gln CAG | Phe TTT | Ile ATC | Ile ATC | MET ATG | Tyr TAT | 2,124 |
| Ser AGT | Leu CTT | Asp GAT | Gly GGG | Lys AAG | Lys AAG | Trp TGG | Gln CAG | Thr ACT | Tyr TAT | Arg CGA | Gly GGA | Asn AAT | Ser TCC | Thr ACT | Gly CCA | Thr ACC | Leu TTA | 2,142 |
| MET ATG | Val GTC | Phe TTC | Phe TTT | Gly GGC | Asn AAT | Val CTC | Asp CAT | Ser TCA | Ser TCT | Gly CCC | Ile ATA | Lys AAA | His CAC | Asn AAT | Ile ATT | Phe TTT | Asn AAC | 2,160 |
| Pro CCT | Pro CCA | Ile ATT | Ile ATT | Ala GCT | Arg CGA | Tyr TAC | Ile ATC | Arg CGT | Leu TTG | His CAC | Pro CCA | Thr ACT | His CAT | Tyr TAT | Ser AGC | Ile ATT | Arg CCC | 2,178 |
| Ser AGC | Thr ACT | Leu CTT | Arg CGC | MET ATG | Glu GAG | Leu TTG | MET ATG | Gly CCC | Cys TGT | Asp GAT | Leu TTA | Asn AAT | Ser ACT | Cys TCC | Ser AGC | MET ATG | Pro CCA | 2,196 |
| Leu TTG | Gly GCA | MET ATG | Glu GAG | Ser AGT | Lys AAA | Ala GCA | Ile ATA | Ser TCA | Asp CAT | Ala GCA | Gln CAG | Ile ATT | Thr ACT | Ala GCT | Ser TCA | Ser TCC | Tyr TAC | 2,214 |

TABLE 1-continued

| | | | | | | | | | | | | | | | | | | |
|---|---|---|---|---|---|---|---|---|---|---|---|---|---|---|---|---|---|---|
| Phe | Thr | Asn | MET | Phe | Ala | Thr | Trp | Ser | Pro | Ser | Lys | Ala | Arg | Leu | His | Leu | Gln | 2,232 |
| TTT | ACC | AAT | ATG | TTT | GCC | ACC | TGG | TCT | CCT | TCA | AAA | GCT | CGA | CTT | CAC | CTC | CAA | |
| Gly | Arg | Ser | Asn | Ala | Trp | Arg | Pro | Gln | Val | Asn | Asn | Pro | Lys | Glu | Trp | Leu | Gly | 2,250 |
| GGG | AGG | ACT | AAT | GCC | TGG | AGA | CCT | CAG | GTG | AAT | AAT | CCA | AAA | CAG | TGG | CTG | CAA | |
| Val | Asp | Phe | Gln | Lys | Thr | MET | Lys | Val | Thr | Gly | Val | Thr | Thr | Gln | Gly | Val | Lys | 2,268 |
| GTG | GAC | TTC | CAG | AAG | ACA | ATG | AAA | CTC | ACA | GGA | GTA | ACT | ACT | CAG | GGA | CTA | AAA | |
| Ser | Leu | Leu | Thr | Ser | MET | Tyr | Val | Lys | Glu | Phe | Leu | Ile | Ser | Ser | Ser | Gln | Asp | 2,286 |
| TCT | CTG | CTT | ACC | ACC | ATG | TAT | GTG | AAG | GAG | TTC | CTC | ATC | TCC | ACC | ACT | CAA | CAT | |
| Gly | His | Gln | Trp | Thr | Leu | Phe | Phe | Gln | Asn | Gly | Lys | Val | Lys | Val | Phe | Gln | Gly | 2,304 |
| GGC | CAT | CAG | TGG | ACT | CTC | TTT | TTT | CAG | AAT | CCC | AAA | CTA | AAC | CTT | TTT | CAG | CCA | |
| Asn | Gln | Asp | Ser | Phe | Thr | Pro | Val | Val | Asn | Ser | Leu | Asp | Pro | Pro | Leu | Leu | Thr | 2,322 |
| AAT | CAA | GAC | TCC | TTC | ACA | CCT | GTG | GTG | AAC | TCT | CTA | GAC | CCA | CCG | TTA | CTG | ACT | |
| Arg | Tyr | Leu | Arg | Ile | His | Pro | Gln | Ser | Trp | Val | His | Gln | Ile | Ala | Leu | Arg | MET | 2,340 |
| CGC | TAC | CTT | CGA | ATT | CAC | CCC | CAG | AGT | TGG | CTC | CAC | CAG | ATT | CCC | CTG | ACC | ATG | |
| Glu | Val | Leu | Gly | Cys | Glu | Ala | Gln | Asp | Leu | Tyr | End | | | | | | | 2,352 |
| GAG | GTT | CTG | GCC | TGC | GAG | GCA | CAG | GAC | CTC | TAC | TGA | GGGTGGCCACTGCATGCCCACCTGCCACTG | | | | | | |

CCGTCACCTCTCCCTCCTCAGCTCCAGGGCATGTGTCCCTCCCTGGCTTGCTTCTACCTTTGTGCTAAATCCTAGCAGACACTCCCTTG
AAGCCTCCTGAATTAACTATCATGACTCCTGCATTTCTTTGGTGGGGGGCCAGGAGGCTGCATCCATTTTAACTTAACTCTTACCTATT
TTCTGCAGCTGCTCCCAGA

By way of example, one compound of this invention contains a region X comprising the amino acid sequence of Ser-760 to Pro-1000 followed by the amino acid sequence of Asp-1582 to Arg-1708. That compound thus comprises the polypeptide sequence of Ala-20 to Pro-1000 covalently linked by a peptide bond to amino acids Asp-1582 to Tyr-2351. Another exemplary compound contains a region X comprising the amino acid sequence Ser-760 to Thr-778 followed by the sequence Pro-1659 to Arg-1708. That compound thus comprises the polypeptide sequence Ala-20 to Thr-778 covalently linked by a peptide bond to the sequence Pro-1659 through Tyr-2351. Still another exemplary compound contains a region X comprising the amino acid sequence Ser-760 to Thr-778 followed by the sequence Glu-1694 to Arg-1708. That compound thus comprises the polypeptide sequence Ala-20 to Thr-778 covalently linked by a peptide bond to amino acids Glu-1694 through Tyr-2351.

These exemplary compounds are depicted schematically in Table 2.

The amino acid sequence represented by X should be selected so that it does not substantially reduce the procoagulant activity of the molecule, which activity can be conveniently assayed by conventional methods. Compound (2) of Table 2 is a presently preferred embodiment.

The procoagulant protein may be produced by appropriate host cells transformed by factor VIII:C DNA which has been specifically altered by use of any of a variety of site-specific mutagenesis techniques which will be familiar to those of ordinary skill in the art of recombinant DNA.

The starting materials may be a DNA sequence which codes for the complete factor VIII:C molecule, e.g., the complete human factor VIII:C as shown in Table 1, a truncated version of that sequence, or it may comprise segments of that DNA sequence, so long as the starting materials contain at least sufficient DNA to code for the amino acid sequences of the desired polypeptide.

the present invention. Moreover, the fact that the procoagulants of the present invention lack many of the sites for non-human glycosylation by the non-human mammalian or other cells used to produce the proteins is also belived to reduce the antigenicity of that protein, and lessen the likelihood of developing antibodies to the procoagulants. This may enable facilitating the treatment of patients in need of procoagulant therapy.

I contemplate that my compounds can be produced by recombinant DNA techniques at a much lower cost than is possible for production of human factor VIII. The host organisms should more efficiently process and express the substantially simpler molecules of this invention.

The compounds of this invention can be formulated into pharmaceutically acceptable preparations with parenterally acceptable vehicles and excipients in accordance with procedures known in the art.

The pharmaceutical preparations of this invention, suitable for parenteral administration, may conveniently comprise a sterile lyophilized preparation of the protein which may be reconstituted by addition of sterile solution to produce solutions preferably isotonic with the blood of the recipient. The preparation may be presented in unit or multi-dose containers, e.g. in sealed ampoules or vials. Their use would be analogous to that of human factor VIII, appropriately adjusted for potency.

One method by which these proteins can be expressed is by use of DNA which is prepared by cutting a full-length factor VIII:C DNA with the appropriate restriction enzymes to remove a portion of the DNA sequence that codes for amino acids 760 to 1708 of human factor VIII:C. The cut DNA is then ligated with an oligonucleotide that resects the cut DNA and maintains the correct translational reading frame.

Preparation of the cDNA has been set forth in detail in U.S. patent applications Ser. Nos. 546,650 and 644,086, supra. A pSP64 recombinant clone containing the nucleotide sequence depicted in Table 1, designated as pSP64-VIII, is on deposit at the American Type

TABLE 2

EXEMPLARY COMPOUNDS A-X-B

| Compound | Amino Acid Sequence | X | Deletion |
|---|---|---|---|
| (human factor VIII:c) | ($Ala_{20}$→$Tyr_{2351}$) | ($Ser_{760}$→$Arg_{1708}$) | 0 |
| 1 | ($Ala_{20}$→$Pro_{1000}$)—($Asp_{1582}$→$Tyr_{2351}$) | ($Ser_{760}$→$Pro_{1000}$)—($Asp_{1582}$→$Arg_{1708}$) | 581 |
| 2 | ($Ala_{20}$→$Thr_{778}$)—($Pro_{1659}$→$Tyr_{2351}$) | ($Ser_{760}$→$Thr_{778}$)—($Pro_{1659}$→$Arg_{1708}$) | 880 |
| 3 | ($Ala_{20}$→$Thr_{778}$)—($Glu_{1694}$→$Tyr_{2351}$) | ($Ser_{760}$→$Thr_{778}$)—($Glu_{1694}$→$Arg_{1708}$) | 915 |

A and B are as defined, supra; "—"represents a peptide bond; "→"indicates a polypeptide sequence inclusive of the specified amino acids; amino acid numbering corresponds to the numbering of the sequence depicted in Table 1; and "deletion"indicates the number of amino acids deleted relative to human factor VII:c.

The procoagulant proteins of the present invention, in addition to lacking a substantial amino acid segment of human factor VIII:C, also have fewer potential N-glycosylation sites than human factor VIII. Preferably, at least one N-glycosylation site has been deleted. More preferably, 18 of the 25 potential N-glycosylation sites are not in the molecule. In still more preferred embodiments, up to 19 of the 25 potential N-glycosylation sites are removed. While not wishing to be bound by theory, it is presently believed that the antibodies to factor VIII:C which are directed to antigenic determinants contained in the protein segment deleted in accordance with this invention, i.e., in the amino acid segement itself or in the carbohydrate portion of the glycosylated protein, will not neutralize the procoagulant proteins of Culture Collection under Accession Number ATCC 39812.

Restriction endonucleases are used to obtain cleavage of the human factor VIII:C cDNA, hereinafter the DNA source sequence, at appropriate sites in the nucleotide sequence. Unless otherwise noted, restriction endonucleases are utilized under the conditions and in the manner recommended by their commercial suppliers. The restriction endonucleases selected herein are those which will enable one to excise with substantial specificity sequences that code for the portion of the factor VIII:C molecule desired to be excised. BamHI and SacI are particularly useful endonucleases. However, the skilled artisan will be able to utilize other restriction endonucleases chosen by conventional selection methods. The number of nucleotides deleted may vary but care should be taken to insure that the reading frame of the ultimate cDNA sequence will not be affected.

The resulting DNA fragments are then purified using conventional techniques such as those set forth in Maniatis et al., *Molecular Cloning, A Laboratory Manual* (Cold Spring Harbor Laboratory 1982) the disclosure of which is incorporated herein by reference, and *Proc. Natl. Acad. Sci.* 76:615–619 (1979). The purified DNA is then ligated to form the sequence encoding the polypeptide of the preferred invention. When necessary or desirable, the ligation may be within an oligonucleotide that resects the cut DNA and maintains the correct translational reading frame using standard ligation conditions. Ligation reactions are carried on as described by Maniatis et al., supra at 2453–6 using the buffer described at page 246 thereof and using a DNA concentration of 1–100 ug/ml, at a temperature of 23° C. for blunt ended DNA and 16° C. for "sticky ended" DNA. The following double-stranded oligonucleotide is useful when there is BamHI/SacI deletion such as described infra,

5'P-CATGGACCG-3'

3-TCGAGTACCTGGCCTAG 5';

but other oligonucleotides can be selected by the skilled artisan depending upon the deletions made and reaction conditions.

The DNA sequences encoding the novel procoagulant polypeptides can, in addition to other methods, be derived from the sequence of human factor VIII:C DNA by application of oligonucleotide-mediated deletion mutagenesis, often referred to as "loopout" mutagenesis, as described for example in Morinaga, Y. et al. *Biotechnology,* 636–639 (1984).

The new DNA sequences containing the various deletions can then be introduced into appropriate vectors for expression in mammalian cells. The procoagulant activity produced by the transiently transfected or stably transformed host cells may be measured by using standard assays for blood plasma samples.

The eukaryotic cell expression vectors described herein may be synthesized by techniques well known to those skilled in this art. The components of the vectors such as the bacterial replicons, selection genes, enhancers, promoters, and the like may be obtained from natural sources or synthesized by known procedures. See Kaufman et al., *J. Mol. Biol.,* 159: 51–521 (1982); Kaufman, *Proc. Natl. Acad. Sci.* 82: 689–693 (1985).

Established cell lines, including transformed cell lines, are suitable as hosts. Normal diploid cells, cell strains derived from in vitro culture of primary tissue, as well as primary explants (including relatively undifferentiated cells such as haematopoeitic stem cells) are also suitable. Candidate cells need not be genotypically deficient in the selection gene so long as the selection gene is dominantly acting.

The host cells preferably will be established mammalian cell lines. For stable integration of the vector DNA into chromosomal DNA, and for subsequent amplification of the integrated vector DNA, CHO (Chinese hamster ovary) cells are presently preferred. See U.S. Pat. No. 4,399,216. Alternatively, the vector DNA could include all or parts of the bovine papilloma virus genome (Lusky et al., *Cell,* 36: 391–401 (1984) and be carried in cell lines such as C127 mouse cells as a stable episomal element. Other usable mammalian cell lines include HeLa, COS-1 monkey cells, melanoma cell lines such as Bowes cells, mouse L-929 cells, 3T3 lines derived from Swiss, Balb-c or NIH mice, BHK or HaK hamster cells lines and the like.

Stable transformants then are screened for expression of the procoagulant product by standard immunological or enzymatic assays. The presence of the DNA encoding the procoagulant proteins may be detected by standard procedures such as Southern blotting. Transient expression of the procoagulant genes during the several days after introduction of the expression vector DNA into suitable host cells such as COS-1 monkey cells is measured without selection by enzymatic or immunologic assay of the proteins in the culture medium.

The invention will be further understood with reference to the following illustrative embodiments, which are purely exemplary, and should not be taken as limiting the true scope of the present invention, as described in the claims.

EXAMPLE 1

10 μg. of the plasmid pACE, a pSP64 (Promega Biotec, Madison, Wis.) derivative, containing nucleotides 562-7269 of human factor VIII:C cDNA (nucleotide 1 is the A of the ATG initiator methionine codon) was subjected to partial BamHI digestion in 100 ul containing 50 mM Tris.HCl ph 8.0, 50 mM $MgCl_2$, and 2.4 units BamHI (New England Biolabs) for 30 minutes at 37° C. The reaction was terminated by the addition of EDTA to 20 mM and then extracted once with phenol, once with chloroform , ethanol precipitated and pelleted by centrifugation. DNA was redissolved, cleaved to completion in 50 ul using 40 units SacI for 1.5 hours at 37° C. DNA was then electrophoresed through a buffered 0.6% agarose gel. An 8.1 kb fragment corresponding to the partial BamHI-SacI fragment of pACE lacking only the sequence corresponding to nucleotides 2992-4774 of the factor VIII:C sequence was purified from the gel using the glass powder technique described in *Proc. Nat. Acad. Sci.* 76: 615–619 (1979). Purified DNA was ligated with 100 pmoles of the following double-stranded oligonucleotide

5'P-CATGGACCG-3'

3'-TCGAGTACCTGGCCTAG 5' using standard ligation conditions. The DNA sequence removed represents the deletion of 584 amino acid sequence beginning with amino acid 998 and continuing through 1581. The oligonucleotide inserted, however, encodes amino acids corresponding to 998–1000. Therefore, the polypeptide encoded contains deletion of 581 amino acids.

DNA was then used to transform competent *E. coli* bacteria, and DNA from several ampicillin resistant transformants was analyzed by restriction mapping to identify a plasmid harboring the desired SacI-BamHI deletion mutant. DNA from this plasmid was digested to completion with KpnI, which cleaves the plasmid uniquely at nucleotide 1816 of the factor VIII:C coding sequence. This DNA was ligated with a KpnI DNA fragment containing nucleotides 1-1815 of factor VIII:C DNA and a synthetic SalI site at nucleotides −11 to −5 and then used to transform competent *E. coli* bacteria.

Plasmid DNA was isolated and oriented by restriction mapping to identify a plasmid, pBSdK, containing the correct 5' to 3' orientation of the KpnI insert. SalI digestion, which excises the entire polypeptide coding region from the plasmid, was performed and the DNA electrophoresed through a buffered 0.6% agarose gel. The 5.3 Kb SalI fragment was purified from the gel as described above. This DNA fragment was ligated with XhoI cut pXMT2 DNA to give rise to plasmid pDGR-2. pXMT2 is a plasmid capable of expressing heterologous genes when introduced into mammalian cells such as the COS-1 African Green Monkey kidney cell line, and is a derivative of the expression vectors described in Kaufman, supra at 689–93. The expression elements are the same as described for plasmid pQ2 except that it contains a deletion of the adenovirus major late promoter extending from −45 to +156 with respect to the transcription start site of the adenovirus major late promoter. mRNA expression in pXMT is driven by the SV40 late promoter. The bacterial replicon, however, has been substituted to render bacteria containing the vector resistant to ampicillin rather than tetracycline. pXMT2 contains a unique Xho I site at a position which allows for expression of inserted cDNA from the SV40 late promoter. This Xho I site is convenient for inserting factor VIII:C cDNA constructs since these are flanked by SalI sites.

Restriction mapping of transformants identified a plasmid, pDGR-2, containing the correct 5' to 3' orientation of the polypeptide coding sequence relative to the direction of transcription from the SV40 late promoter. pDGR-2 is on deposit at the American Type Culture Collection under Accession number 53100.

EXAMPLE 2

Other novel procoagulant proteins may be obtained from constructs produced by oligonucleotide mediated deletion mutagenesis, using for example the "loopout" mutagenesis techniques as described in Morinaga et al., supra. The deletion mutagenesis is performed using expression plasmid pDGR-2 or any other appropriate plasmid or bacteriophage vector. Other methods for oligonucleotide mediated mutagenesis employing single stranded DNA produced with M13 vectors and the like are also suitable. See Zoller et al., *Nucl. Acids Res.* 10: 648–6500 (1982). For example, these deletions can be produced using the oligonucleotides (A) 5'
AAAAGCAATTTAATGCCACCCCAC-
CAGTCTTGAAACGCCA (B) 5'
AAAAGCAATTTAATGCCACC-
GAAGATTTTGACATTTATGA to cause deletions in factor VIII:C cDNA from nucleotides (A) 2334 to 4974 or (B) 2334 to 5079. The proteins encoded by these constructs contain deletions of (A) 880 and (B) 915 amino acids relative to Factor VIII:C.

The deleted constructs are tested directly, or after subcloning into appropriate expression vectors, in order to determine if the novel proteins possess procoagulant activity. Procoagulant activity was assayed as described in Examples 3 and 4.

EXAMPLE 3

Expression of Procoagulant Molecules in COS Monkey Cells The expression plasmids containing the modified cDNA's prepared as in Examples 1 or 2 and the full-length cDNA, pXMT-VIII, were introduced into COS-1 cells via the DEAE-dextran transfection protocol. Sompayrac and Dana 1981, *Proc. Natl. Acad. Sci.* 78: 7575–7578. Conditioned media was harvested 48 hours post-transfection and assayed for factor VIII-type activity as described in Toole et. al., 1984, *Nature* 312:342–347. The results of the experiment are summarized in Table 3. Both plasmids containing the modified cDNAs yielded procoagulant activity and, moreover, the activity was greater than that obtained using wild type cDNA. From these data it was concluded that removal of up to 880 amino acids (95,000 daltons) in a defined domain of human factor VIII does not destroy cofactor activity. Furthermore, these abridged procoagulant proteins retain their ability to be activated by thrombin.

TABLE 3

EXPRESSION OF ABRIDGED FACTOR VIII MOLECULES

| plasmid | # amino acids deleted | chromogenic activity ($mUml^{-1}$) | Clotek activity −IIa | +IIa (fold) |
|---|---|---|---|---|
| No DNA | | 0 | | |
| pXMT-VIII | — | 15:1 | — | 450 |
| pDGR-2 | 581 | 114 | 250 | 5750 (23X) |
| pLA-2 | 880 | 162 | 330 | 9240 (28X) |

The plasmids indicated were transfected into COS cells and 48 hr. post-transfection the conditioned media taken for assay by the Kabi Coatest factor VIII:C method (chromogenic activity) and by the one-stage activated partial thromboplastin time (APTT) coagulation assay (Clotek activity) using factor VIII:C deficient plasma as described (Toole, *Nature* 1984). For thrombin (IIa) activation, samples were pretreated 1–10 min, with 0.2 units/ml thrombin (IIa) at room temperature. Activation coefficients are provided in parentheses. Activity from media from the wild-type (pXMT-VIII) transfection was too low to directly measure Clotek activity before thrombin activation. From other experiments where the wild type factor VIII activity was concentrated, it was demonstrated to be approximately 30-fold activatable.

EXAMPLE 4

Expression of Procoagulant Molecules in CHO Cells (A) Expression of pDGR-2

The procoagulant expression vector containing a deletion (relative to the Factor VIII:C cDNA) of 581 amino acids (pDGR-2) was transfected with plasmid pAdD26SV(A)#3 (10 ug pDGR-2:1 ug pAdD26SV-(A)#3) by $CaPO_4$ coprecipitatio CHO DHFR deficient cells (DUKX-B11) and transformants isolated and grown in increasing concentrations of MTX as described by Kaufman et. al., (1985). One transformant designated J1 exhibited the following activities as a function of resistance to increasing concentrations of MTX.

| uM MTX | mUnits/ml/day/$10^6$ cells* |
|---|---|
| 0 | 1.46 |
| 0.02 | 322 |
| 0.1 | 499 |

(B) Expression of pLA-2

The procoagulant expression vector containing a deletion of 880 amino acids (pLA-2) was introduced into CHO DHFR deficient cells (DUKX-B11, Chasin and Urlaub, PNAS 77: 4216–4220, 1980 by protoplast fusion as described (Sandri-Goldin et al. Mol. Cell. Biol. 1: 743–752). After fusion, fresh medium containing 100 ug/ml of kanamycin, and 10 ug/ml of each of thymidine, adenosine, deoxyadenosine, penicillin, and streptomycin and 10% dialyzed fetal calf serum was added to each plate. The kanamycin was included to prevent the growth of any bacteria which had escaped conversion to protoplasts. Four days later the cells were subcultured 1:15 into alpha-media with 10% dialyzed fetal calf serum, penicillin, and streptomycin, but lacking the nucleosides. Colonies appeared after 10–12 days after subculturing cells into selective media. A group of 8 transformants were pooled and grown in sequentially increasing concentrations of MTX starting at 0.02 uM with steps to 0.1, 0.2, and 1.0 uM MTX (LA 3-5 cells; ATCC No. CRL 10/01). Results of factor VIII-type activity in cells resistant to increasing concentrations of MTX is shown below.

| uM MTX | mUnits/ml/day/$10^6$ cells* |
|---|---|
| 0 | 16 |
| 0.02 | 530 |
| 0.2 | 1170 |
| 1.0 | 1890 |

*Factor VIII activity was determined by the Kabi Coatest factor VIII:C method (chromogenic activity).

What is claimed is:

1. A recombinant DNA which upon expression results in a truncated Factor VIII protein which is an active procoagulant wherein the recombinant DNA encodes for a protein having the amino acid sequence of a human Factor VIII:C except for having a deletion corresponding to at least 581 amino acids within the region between Arg-759 and Ser.-1709, wherein the amino acid numbering is with reference to Met-1 of the human Factor VIII:C leader sequence.

2. The recombinant DNA of claim 1 wherein the deletion corresponds to the region between Pro-1000 and Asp-1582.

3. The recombinant DNA of claim 1 wherein the deletion corresponds to the region between Thr-778 and Pro-1659.

4. The recombinant DNA of claim 1 wherein the deletion corresponds to the region between Thr-778 and Glu-1694.

5. A genetically engineered mammalian host cell containing, and capable of expressing, DNA of claim 1.

6. A genetically engineered mammalian host cell containing, and capable of expressing, DNA of claim 2.

7. A genetically engineered mammalian host cell containing, and capable of expressing, DNA of claim 3.

8. A genetically engineered mammalian host cell containing, and capable of expressing, DNA of claim 4.

9. A method for producing a truncated Factor VIII:C protein which is an active procoagulant having the amino acid sequence of a human Factor VIII:C but lacking at least 581 amino acids of the region between Arg-759 and Ser-1709 which comprises producing a genetically engineered mammalian host cell of claim 5 and culturing said host cell under condition permitting expression of the protein.

10. A truncated human Factor VIII:C protein which is an active procoagulant protein having a peptide sequence of human Factor VIII:C but lacking a peptide region selected from the group consisting of:

(a) the region between Pro-1000 and Asp-1582;

(b) the region between Thr-778 and Pro-1659; and, (c) the region between Thr-778 and Glu-1694.

11. A pharmaceutical preparation for the treatment of Hemphilia A comprising a sterile preparation containing an effective amount of a protein of claim 9, in admixture with a pharmaceutically accepted carrier.

12. A method for treating Hemophilia A comprising administering to a patient a pharmaceutical preparation of claim 11.

* * * * *

UNITED STATES PATENT AND TRADEMARK OFFICE

CERTIFICATE OF CORRECTION

PATENT NO. : 4,868,112

DATED : Sep. 19, 1989

INVENTOR(S) : John J. Toole, Jr.

It is certified that error appears in the above-identified patent and that said Letters Patent is hereby corrected as shown below:

In column 1, between lines 7 and 8 (before the second paragraph), insert the following:

-- This invention was made with Government support under DHHS grant S R44 HL35946-03 awarded by the NIH. The Government has certain rights under the invention. --.

Signed and Sealed this

Third Day of November, 1992

Attest:

DOUGLAS B. COMER

*Attesting Officer*

*Acting Commissioner of Patents and Trademarks*